United States Patent
Slazas et al.

(10) Patent No.: US 10,278,848 B1
(45) Date of Patent: May 7, 2019

(54) STENT DELIVERY WITH EXPANSION ASSISTING DELIVERY WIRE

(71) Applicant: DePuy Synthes Products, Inc., Raynham, MA (US)

(72) Inventors: Robert Slazas, Raynham, MA (US); Juan Lorenzo, Raynham, MA (US); Lacey Gorochow, Raynham, MA (US); Pedro Pedroso, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/056,065

(22) Filed: Aug. 6, 2018

(51) Int. Cl.
  *A61F 2/06* (2013.01)
  *A61F 2/95* (2013.01)
  *A61F 2/90* (2013.01)

(52) U.S. Cl.
  CPC ............ *A61F 2/95* (2013.01); *A61F 2/90* (2013.01); *A61F 2002/9505* (2013.01); *A61F 2210/0014* (2013.01); *A61F 2250/0098* (2013.01)

(58) Field of Classification Search
  CPC .......... A61F 2/95; A61F 2/9505; A61F 2/962; A61F 2/966; A61F 2002/9522; A61F 2002/9534; A61F 2002/9665
  See application file for complete search history.

(56) References Cited

U.S. PATENT DOCUMENTS

| | | | |
|---|---|---|---|
| 8,048,139 B2 * | 11/2011 | Frid | A61F 2/90 623/1.11 |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,775,706 B2 | 3/2017 | Peterson | |
| 9,615,832 B2 | 4/2017 | Bose et al. | |
| 9,615,951 B2 | 4/2017 | Bennett et al. | |
| 9,622,753 B2 | 4/2017 | Cox | |

(Continued)

*Primary Examiner* — Melanie R Tyson
(74) *Attorney, Agent, or Firm* — Troutman Sanders LLP

(57) ABSTRACT

An expandable element having a distal anchor member at a distal end, a proximal anchor member at a proximal end, and a braided intermediate portion can be delivered to a treatment site through a catheter by a delivery wire having a first, distal bump that can be translated distally to push the distal anchor distally and release the distal anchor upon exiting a distal end of the catheter, a shaped segment that can be moved to apply a radial force from within the braided intermediate portion to expand the braided intermediate portion, and a second, proximal bump that can be translated distally to push the proximal anchor distally and expel the expandable element from the catheter. The delivery wire can also have a third, recapture bump positioned between the proximal and distal bumps that can be translated proximally to retract a partially implanted expandable element into the catheter.

11 Claims, 14 Drawing Sheets

(56) References Cited

U.S. PATENT DOCUMENTS

| | | |
|---|---|---|
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |

\* cited by examiner

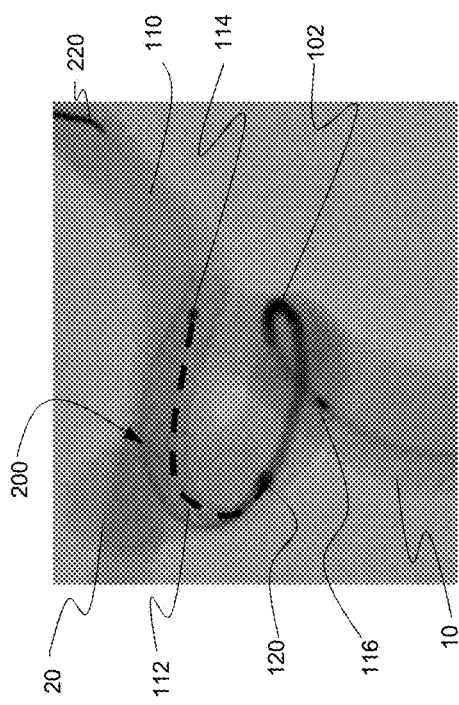
FIG. 6A
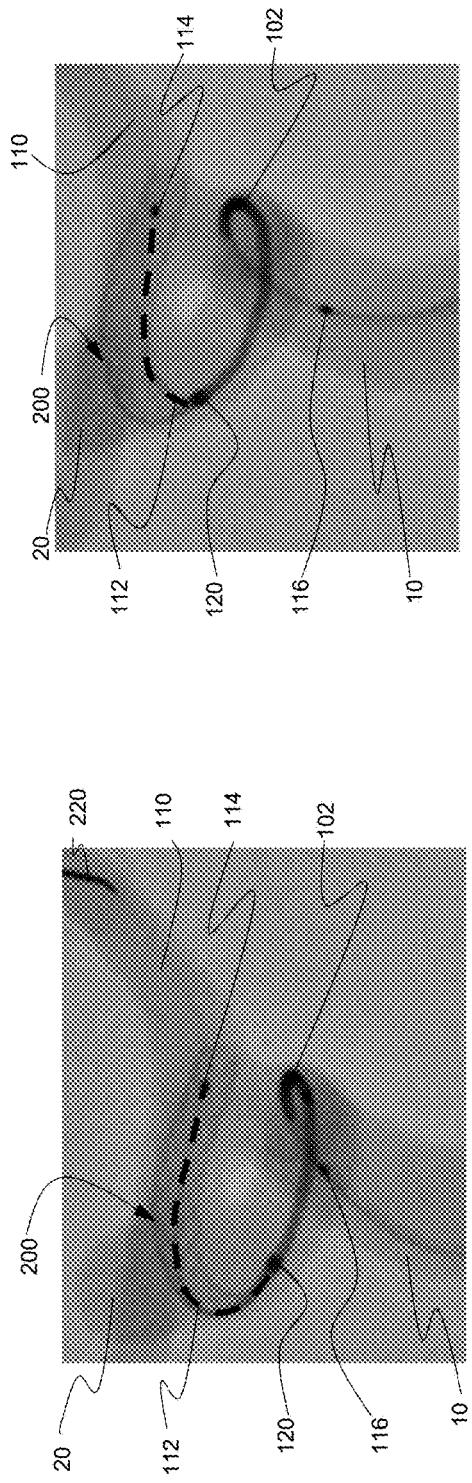
FIG. 6B
FIG. 6C

STENT DELIVERY WITH EXPANSION ASSISTING DELIVERY WIRE

FIELD OF INVENTION

The present invention generally relates to devices for interventional therapeutic treatment or vascular surgery for treatment of defects in the vasculature, and more particularly to delivering a stent to a treatment site in a body lumen of a patient and opening the stent at the treatment site.

BACKGROUND

Stents are inserted into a blood vessel to provide an open path within the blood vessel, and they have been widely used intravascular angioplasty treatment of occluded blood vessels and other applications. Stents can be self-expanding or can be expanded by a radial force applied from inside the stent, for example when the stent is fitted with a balloon.

A braided stent can be characterized by a tube of metal wires woven together with a plain weaving technique. During delivery to a treatment site, a braided stent can travel through a catheter in an elongated, collapsed configuration, having a small diameter, and the braided stent can enlarge in diameter at a treatment site. Proper treatment with a braided stent can require that the stent extend radially to the walls of the body lumen in which the stent is implanted. Although braided stents can be self-expanding, such implants typically open with low opening forces, and therefore may not fully open to conform to a vessel wall. Post deployment, ancillary devices such as guidewires, catheters, balloons, etc. can be used to cross the braid and attempt to further expand the braided stent to improve vessel wall conformity. Issues such as unintentional braid movement or inability to fully open the braid commonly occur. Further, a braided implant that is separated from a delivery wire cannot be recovered for repositioning.

SUMMARY

It is an object of the present invention to provide systems, devices, and methods for improving vessel wall conformity of a braided stent. Generally, an expandable element having a distal anchor member at a distal end, a proximal anchor member at a proximal end, and a braided intermediate portion can be delivered to a treatment site through a catheter by a delivery wire having a first, distal bump that can be translated distally to push the distal anchor distally and release the distal anchor upon exiting a distal end of the catheter, a shaped segment that can be moved to apply a radial force from within the braided intermediate portion to expand the braided intermediate portion, and a second, proximal bump that can be translated distally to push the proximal anchor distally and expel the expandable element from the catheter.

The delivery wire can also have a third, recapture bump positioned proximal the distal bump and distal the proximal bump that can be translated proximally to push the proximal anchor proximally. A partially implanted expandable element having a distal portion expelled from the catheter and released from the delivery wire and a proximal anchor positioned within the catheter can be retracted by translating the delivery wire proximally to push the proximal anchor proximally, thereby pulling the braided portion and distal anchor proximally into the catheter.

An example vascular treatment apparatus can include a catheter, an expandable element, and a delivery wire. The catheter can have an inner lumen through which the expandable element can be delivered by the delivery wire to a treatment site. The expandable element can have a proximal end, a distal end, a braided portion located between the proximal end and the distal end, a proximal anchor member disposed at the proximal end, and a distal anchor member disposed at the distal end.

The expandable element can have a compressed configuration dimensioned to fit within the inner lumen of the catheter for delivery to the treatment site and a partially implanted configuration when the expandable element is not fully implanted at the treatment site. In the partially implanted configuration, the proximal end of the expandable element can be dimensioned to fit within the inner lumen of the catheter, and the distal end can be dimensioned larger than the catheter.

The delivery wire can be disposed within and extend through the inner lumen of the catheter and the expandable element, the expandable element having a substantially tubular shape. The delivery wire can have a proximal portion, a proximal bump member located at a distal end of the proximal portion, a distal portion, a distal bump member located at a proximal end of the distal portion, and a shapeable portion located between the proximal bump member and the distal bump. The shapeable portion can be movable from a substantially straight configuration to a curved configuration upon exiting the inner lumen of the catheter.

The expandable element can be movable from the compressed configuration to the partially implanted configuration by a distal movement of the delivery wire which can cause the distal bump member of the delivery wire to engage with the distal anchor member of the expandable element and push the distal anchor member distally. The distal anchor member can be expelled from the catheter pushing the distal anchor member out of the catheter with the distal bump member.

The delivery wire can be moved distally, proximally, and rotationally in relation to the expandable element in the partially implanted configuration, and the shapeable portion of the delivery wire can be moved to provide a radial force from within the braided portion of the expandable element when the expandable element is in the partially implanted configuration.

The shapeable portion can be movable to at least one of a symmetrical arc shape, an asymmetrical arc shape, or an approximate "S" shape in the curved configuration.

The expandable element can be in the compressed configuration and positioned entirely within the inner lumen of the catheter. When the expandable element is in the compressed configuration and positioned entirely within the inner lumen of the catheter, the shaped portion can be in the substantially straight configuration and can be positioned within a lumen of the braided portion of the expandable element, the distal bump member can be positioned within the lumen of the braided portion of the expandable element, and the proximal bump member can be positioned proximal the proximal anchor member.

The expandable element can be in the partially implanted configuration such that the distal end of the expandable element is positioned outside the catheter and the proximal end and the proximal anchor of the expandable element are positioned within the inner lumen of the catheter. When the expandable element is in the partially implanted configuration, the shapeable portion of the delivery wire can be in the curved configuration and positioned outside the catheter, and a rotation of the delivery wire in relation to the expandable element can expand a radius of the expandable element.

An example method for implanting a stent can include the steps of: providing an implantation system comprising a catheter, an expandable element, and a delivery wire; moving a first portion of the expandable element to exit the catheter; maintaining a second portion of the expandable element within the catheter to establish a partially implanted configuration; moving the delivery wire independent of the expandable element in the partially implanted configuration; and enlarging a circumference of the expandable element in response to the moving the delivery wire. The method can further include the steps of positioning a proximal anchor at a proximal end of the expandable element; positioning a distal anchor at a distal end of the expandable element; positioning a distal bump on the delivery wire; positioning a proximal bump on the delivery wire proximal to the distal bump; positioning the distal bump within a lumen of the expandable element; positioning the proximal bump proximal to the expandable element; positioning the expandable element and at least a portion of the delivery wire within a lumen of the catheter; and moving the distal anchor and the expandable element distally through the lumen of the catheter by pushing the delivery wire distally thereby pushing the distal bump against the distal anchor; expelling the proximal anchor from the distal end of the catheter by pushing the delivery wire distally thereby pushing the proximal bump against the proximal anchor; and expanding the expelled proximal anchor.

The step of moving a first portion of the expandable element to exit the catheter can include the steps of expelling the distal anchor from a distal end of the catheter by pushing the delivery wire distally thereby pushing the distal bump against the distal anchor; and expanding the expelled distal anchor.

The step of moving the delivery wire independent of the expandable element in the partially implanted configuration can include the step of maintaining the proximal anchor within the lumen of the catheter.

The step of enlarging a circumference of the expandable element in response to the moving the delivery wire can include the step of providing a radial force from the delivery wire against the expandable element from within the lumen of the expandable element.

The method can further include the steps of shaping a portion of the delivery wire from a substantially straight configuration to a curved configuration upon a distal movement of the portion from within the lumen of the catheter to a position outside the lumen of the catheter; sliding the shaped portion of the delivery wire against the expandable element from within the lumen of the expandable element; extending a portion of the expandable element to a wall of a vascular by moving the shaped portion against the expandable element; and moving the second portion of the expandable element to exit the catheter and become implanted by pushing the expandable element distally with a distal movement of the delivery wire.

An example system for implanting a stent or other such expandable element can include a catheter, a braided stent, and a delivery wire. The braided stent can be movable to a partially implanted configuration characterized by a portion of the braided stent exterior to the catheter and a portion of the braided stent within the catheter, and the delivery wire can be movable independent of the braided stent and movable to provide a force to open the braided stent when the braided stent is in a partially implanted configuration.

The braided stent can be moved in a compressed configuration through the catheter and can be movable from the compressed configuration to the partially implanted configuration. The braided stent of the system can have a first expandable anchor at a distal end and a second expandable anchor at a proximal end, such that, in the partially implanted configuration, the first expandable anchor is expanded in an implanted position distal to the catheter and the second expandable anchor is compressed within the catheter.

The delivery wire can be movable in a distal direction, a proximal direction, and in a rotational direction independent of the braided stent when the braided stent is in the partially implanted configuration. The delivery wire can extend through the braided stent when the braided stent is in the compressed configuration and when the braided stent is in the partially implanted configuration.

The delivery wire can include a pusher bump that can be positioned proximal the second expandable anchor when the braided stent is in the compressed configuration and when the braided stent is in the partially implanted configuration. The pusher bump can be movable to push the second expandable anchor distally thereby pushing the braided stent distally when the braided stent is in the partially implanted configuration.

The delivery wire can include a shapeable segment that can be positioned within the braided stent when the braided stent is in the compressed configuration and when the braided stent is in the partially implanted configuration. The shapeable segment can be movable from a substantially straight configuration when the braided stent is in the compressed configuration to a curved configuration when the braided stent is in the partially implanted configuration, and the shapeable segment can be movable independent of the braided stent when the braided stent is in the partially implanted configuration. The shapeable segment can be movable to form an arc shape, an undulating shape, or other atraumatic shape when in the curved configuration.

The delivery wire can include a puller bump positioned distal the pusher bump and the shapeable segment and also positioned proximal the first expandable anchor when the braided stent is in the compressed configuration.

BRIEF DESCRIPTION OF THE DRAWINGS

The above and further aspects of this invention are further discussed with reference to the following description in conjunction with the accompanying Figures, in which like numerals indicate like structural elements and features in various Figures. Images and drawings in the Figures are not necessarily to scale, emphasis instead being placed upon illustrating principles of the invention. As indicated, the Figures depict one or more implementations of the inventive devices, by way of example only, not by way of limitation.

FIGS. 6A to 6C are images illustrating steps for use of an implantation system according to the present invention.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
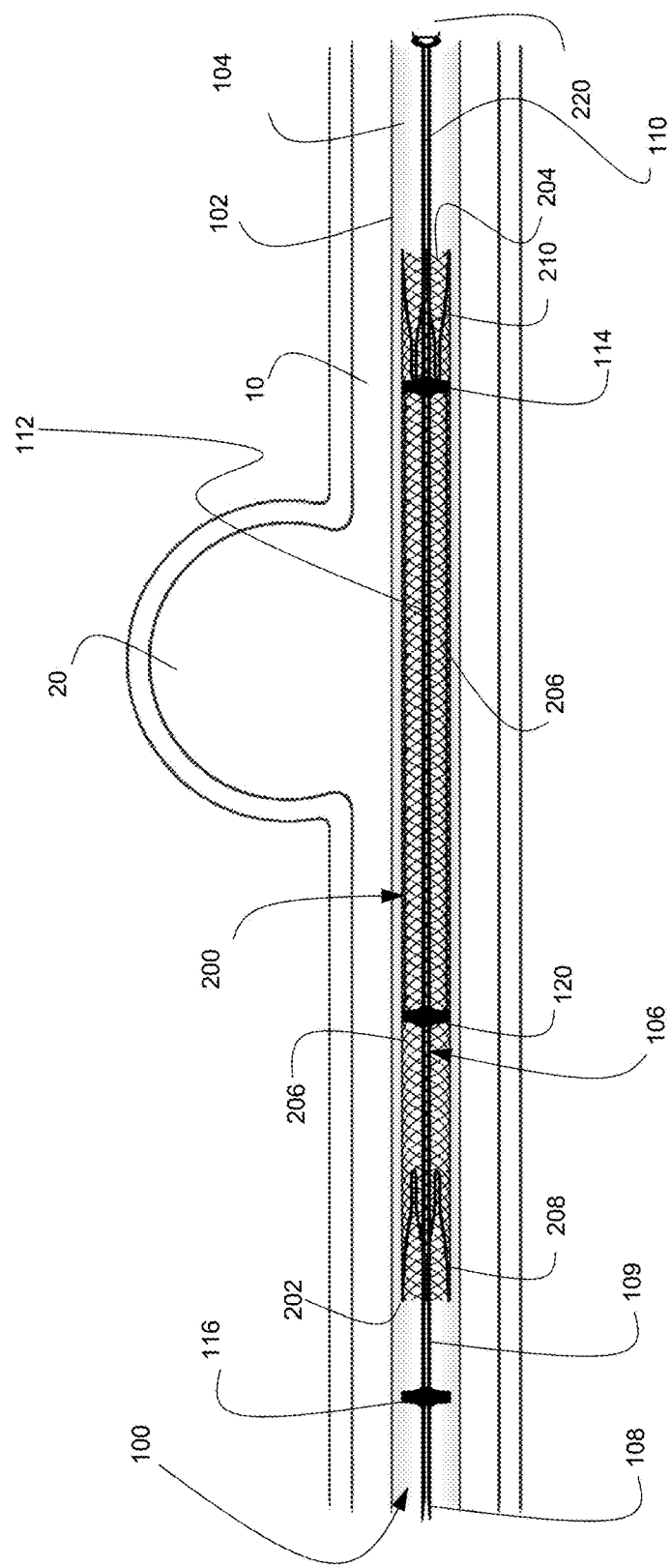
FIG. 1 is a drawing depicting an implantation system in a delivery configuration according to the present invention.

An example of an implantation system 100, as illustrated in FIG. 1 can have a catheter 102, an expandable element 200, and a delivery wire 106. The catheter 102 can have an inner lumen 104, and the expandable element 200 can be formed into a compressed configuration that is dimensioned to fit within the inner lumen 104 of the catheter 102. The expandable element 200 can have a proximal end 202, a distal end 204, a braided portion 206 located between the proximal end 202 and the distal end 204, a proximal anchor member 208 disposed at the proximal end 202, and a distal anchor member 210 disposed at the distal end 204. The delivery wire 106 can be disposed within and extend through the inner lumen 104 of the catheter 102 and the expandable element 200 and can be used to deliver the expandable element 200 to a treatment site and position the expandable element 200 at the treatment site. The delivery wire 106 can have a proximal portion 108, a distal portion 110, a proximal bump member 114 located at a distal end of the proximal portion 108, a distal bump member 114 located at a proximal end of the distal portion 110, and a shapeable portion 112 located between the proximal bump member 116 and the distal bump member 114. When the expandable element 200 is in the compressed configuration for delivery through the catheter 102, the shapeable portion 112 can have a substantially straight shape that has flexibility to navigate through a catheter 102 to a treatment site.

The delivery wire 106 can further include a recapture bump 120 positioned between the distal bump 114 and the proximal bump 116. Delivery, positioning, retraction of an expandable element such as a stent within a body lumen utilizing a delivery wire having a distal bump member, proximal bump member, and a recapture bump is the subject of another patent application filed concurrently with this application.

One or all of the bump members 114, 116, 120 can include a radiopaque material to allow the location of the bumps 144, 116, 120 to be readily visible during an implanting procedure.

The one or more anchor members 208, 210, can be projections which extend generally parallel to a longitudinal axis of the expandable element 200 and extend downward toward the longitudinal axis of the expandable element 200. The anchor members 208, 210 can serve as a radiopaque marker for improved visualization during the deployment of the expandable element 200 within the body lumen 10. The anchor members 208, 210 can be used to align the expandable element 200 so it can be pushed and pulled through the catheter 102 without damage or deformation. The anchor members 208, 210 can also be used to move the braided portion 206 into an expanded/implanted configuration. An example of the anchor member 208, 210 can be found in U.S. Ser. No. 15/299,918, the entirety of which is incorporated herein by reference.

Typically, the expandable element 200 can have a compressed configuration and an expanded, implanted, configuration. In the compressed configuration the expandable element 200 can be dimensioned to fit within the inner lumen 104 of the catheter 102. In certain examples, the catheter 102 can aid in constraining the expandable element 200 so it does not expand when contained within the catheter 102. Other elements can be used to constrain the expandable element 200 as are known in the art.

The expandable element 200 can also have a partially implanted configuration where the proximal end 202 is dimensioned to fit within the inner lumen 104 of the catheter 102 and the distal end 204 is dimensioned larger than the catheter 102.

Figure 2A:
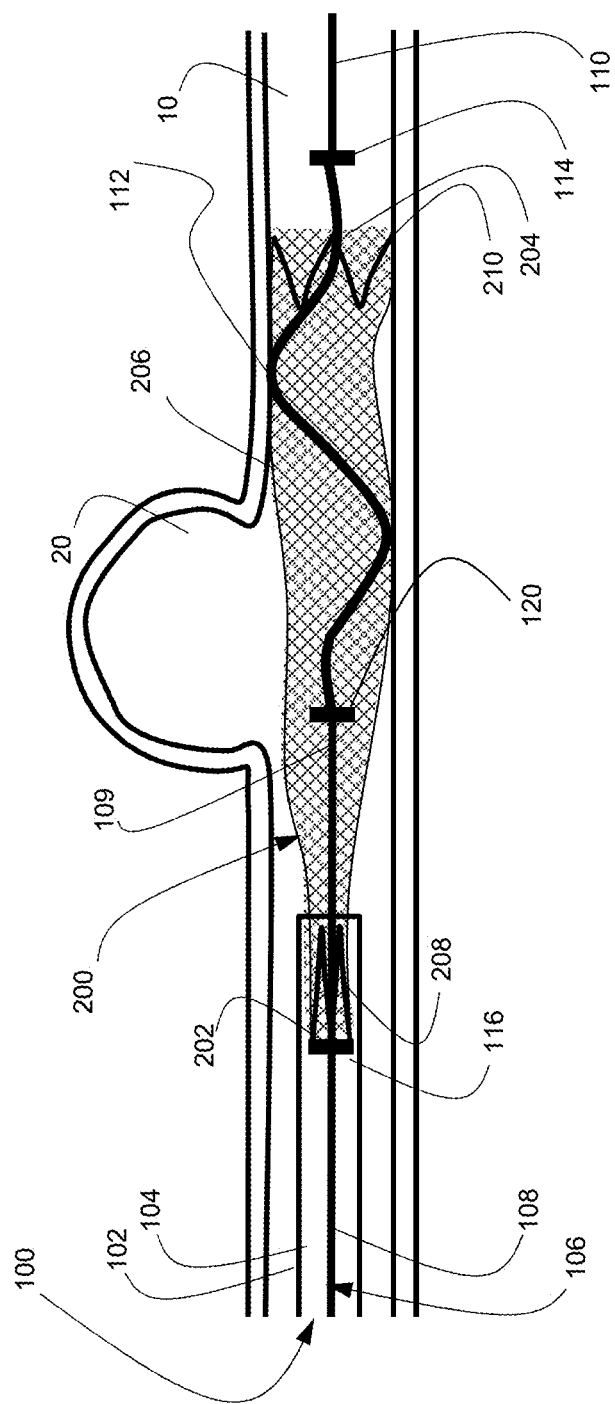
FIGS. 2A to 2H are drawings illustrating steps for use of an implantation system according to the present invention.

FIGS. 2A to 2H are drawings illustrating steps for use of an implantation system. When the expandable element 200 is in the collapsed configuration, the distal bump 114 can be positioned inside the expandable element 200 such that a distal movement of the delivery wire 106 can cause the distal bump 114 to push against the distal anchor 210, pulling the expandable anchor 200 through the catheter 102 to a treatment site. The distal bump member 114 can push the distal anchor member 210 to expel the distal anchor member 210 from the catheter 102, thereby moving the expandable element 200 to a partially implanted configuration as illustrated in FIG. 2A.

Upon exiting the catheter, the shapeable portion 112 of the delivery wire 106 can move from a straight shape to a curved shape as illustrated in FIGS. 2A to 2H. The shapeable portion 112 can provide a radial force from within the braided portion 206 of the expandable element 200 when the expandable element is in the partially implanted configuration.

In an example, the entire delivery wire 106, including the shapeable portion 112, can be made of stainless steel. In other examples, the delivery wire 106 and/or the shapeable portion 112 can be made of a memory shape material including a memory shape metal such as Nitinol or a polymeric memory shape material. The shapeable portion 112 can move from a substantially straight flexible configuration while in the catheter 102 to a curved configuration upon contacting bodily fluid when exiting the catheter 102. Additionally or alternatively, the shapeable portion 112 can curve to conform to the shape of a curved bodily lumen such that distal and proximal movements of the expandable element 200, delivery wire 106, and catheter 102 can cause the delivery wire 106 to move to provide a radial force from within the braided portion 206.

As illustrated in FIG. 2A, during treatment, because self-expanding braided implants may provide a low radial force during implantation, at least some of the intermediate portion 206 of the expandable element 200 may not fully conform to the walls of a body lumen 10.

Figure 2B:
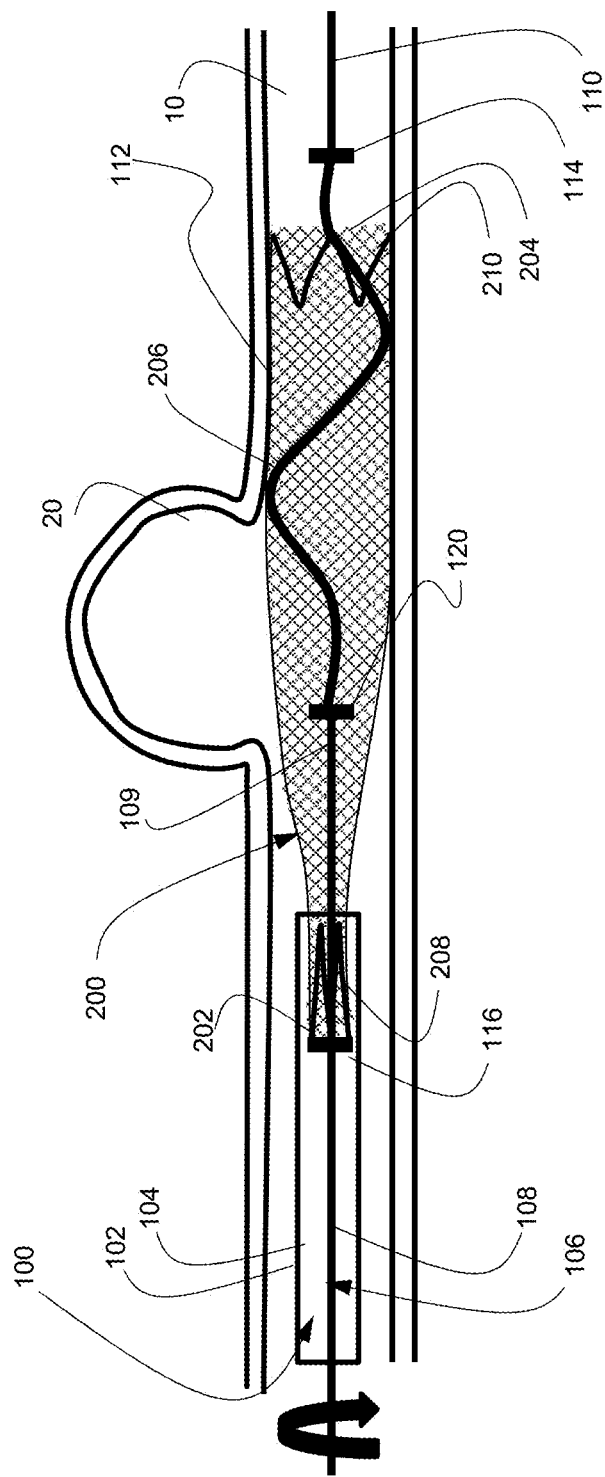

As illustrated in FIG. 2B, the delivery wire 106 can be rotatable in relation to the expandable element 200, and the rotation can cause the shaped portion 112 of the delivery wire 106 to provide a force against the expandable element 200, pushing portions of the expandable element to conform to the walls of the body lumen 10.

Figure 2C:
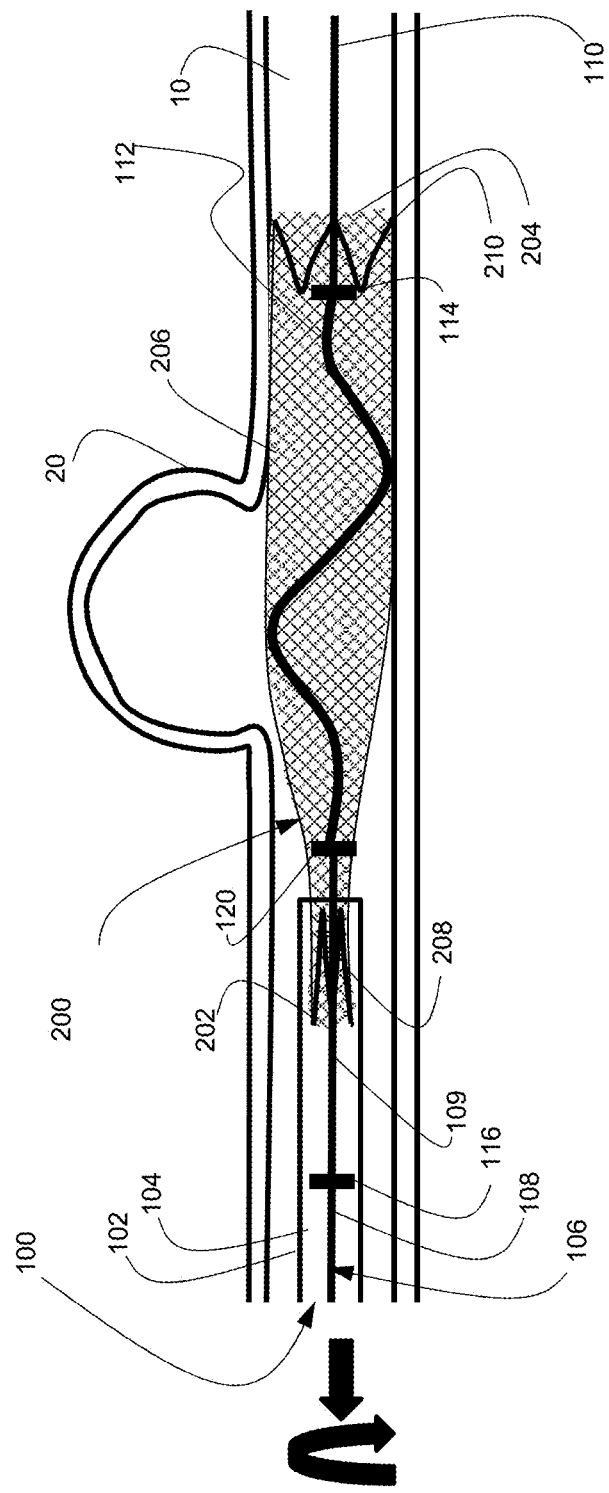

As illustrated in FIG. 2C, the delivery wire 106 can be movable in a distal and a proximal direction in relation to the expandable element 200 without disturbing the placement of the partially implanted expandable element 200. The distal and proximal movement can also cause the shaped portion 112 of the delivery wire 106 to move against the expandable element 200, causing portions of the expandable element 200 to better conform to the walls of the body lumen 10.

Figure 2D:
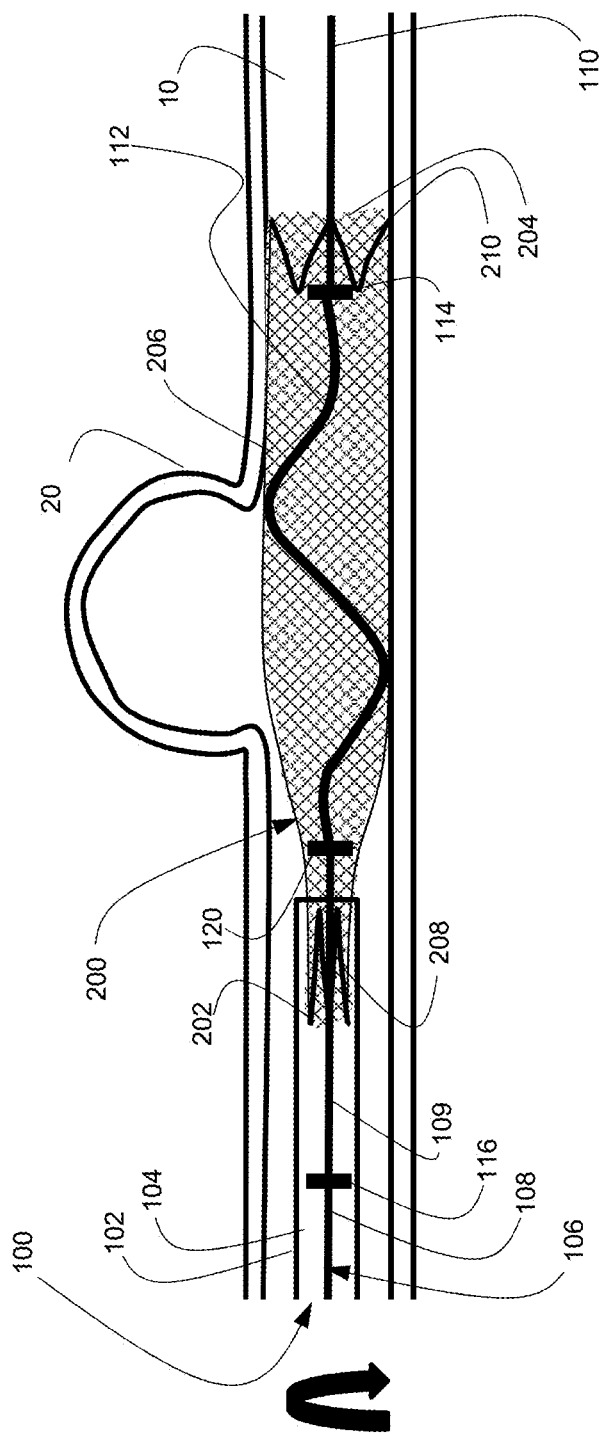

As illustrated in FIG. 2D, the delivery wire 106 can be subsequently rotated to improve conformity of the expandable element 200 to the walls of the body lumen 10.

Figure 2E:
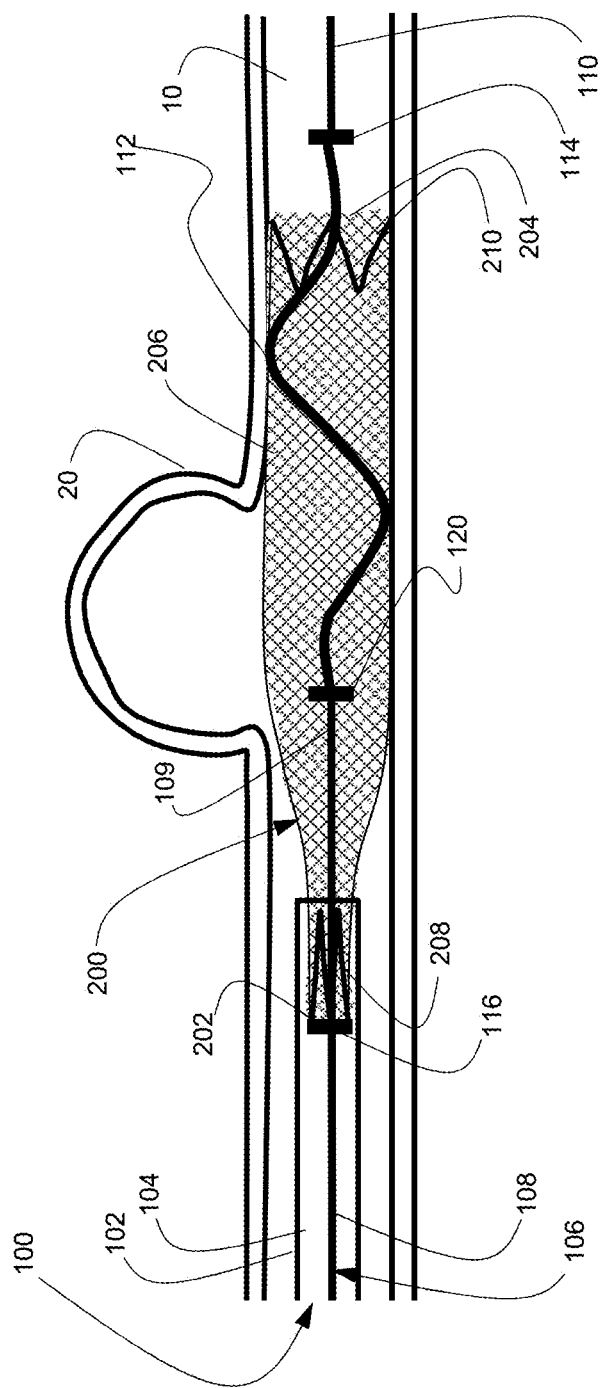

As illustrated in FIG. 2E, when the expandable element 200 is in the partially implanted configuration, the delivery wire 106 can further be moved distally to engage the proximal, pusher bump 116 with the proximal anchor 208.

Figure 2F:
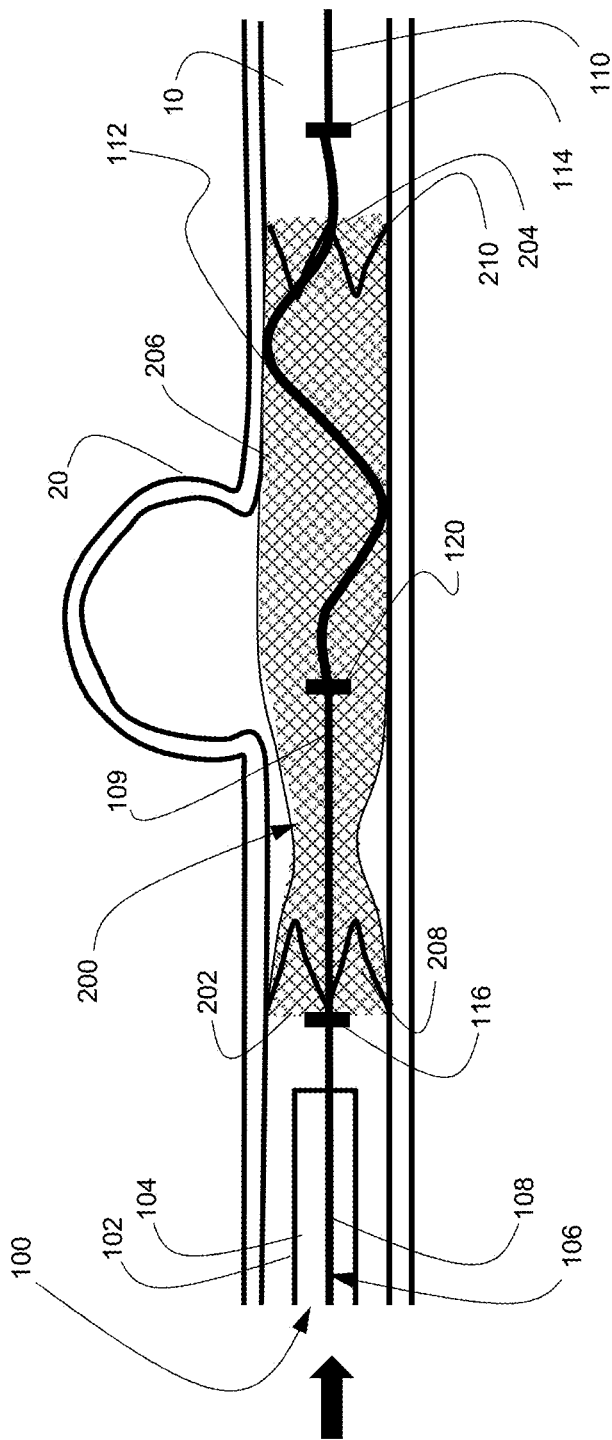

As illustrated in FIG. 2F, further distal movement of the delivery wire 106 can expel the proximal anchor 208 from the catheter 102. Once the proximal anchor 208 is expelled from the catheter 102, the proximal anchor can expand to engage the walls of the body lumen 10. Once the proximal anchor 208 is expanded, the expandable element 200 can be disengaged from the delivery wire 106. As illustrated in FIG. 2F, portions of the expandable element 200 may remain not completely conforming to the walls of the body lumen 10.

Figure 2G:
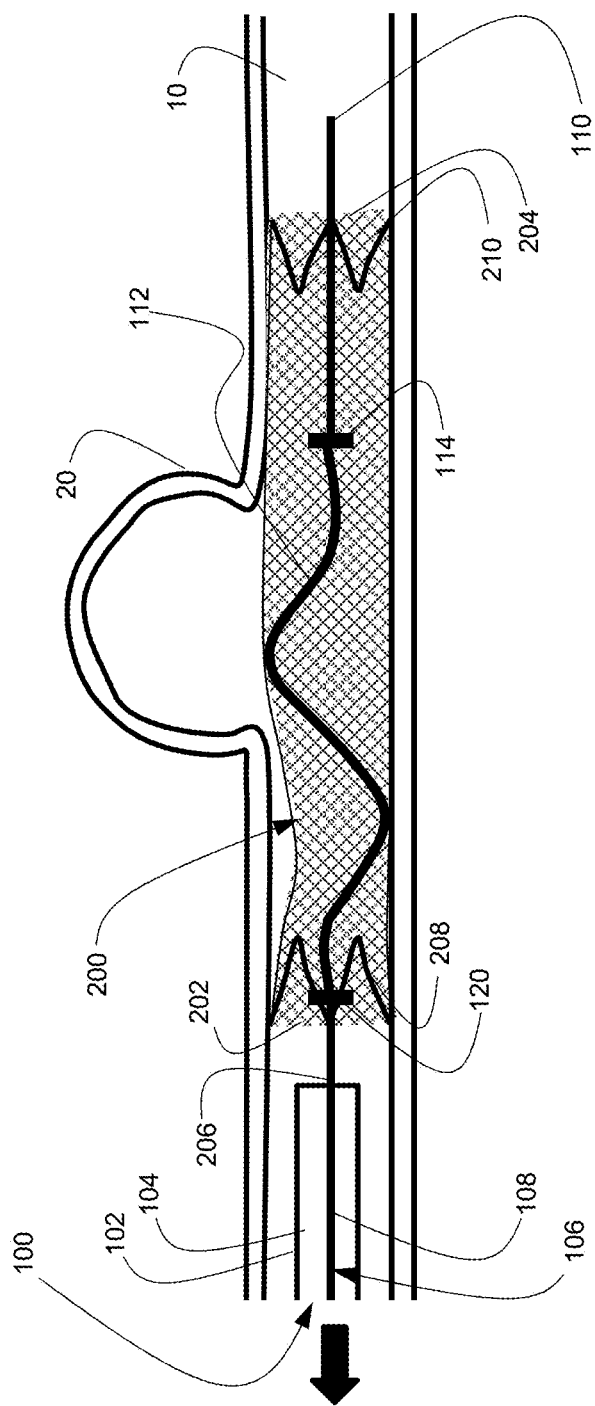

As illustrated in FIG. 2G, the delivery wire 106 can subsequently be moved proximally to side against portions of the braid, resulting in better conformity to the walls of the body lumen 10.

Figure 2H:
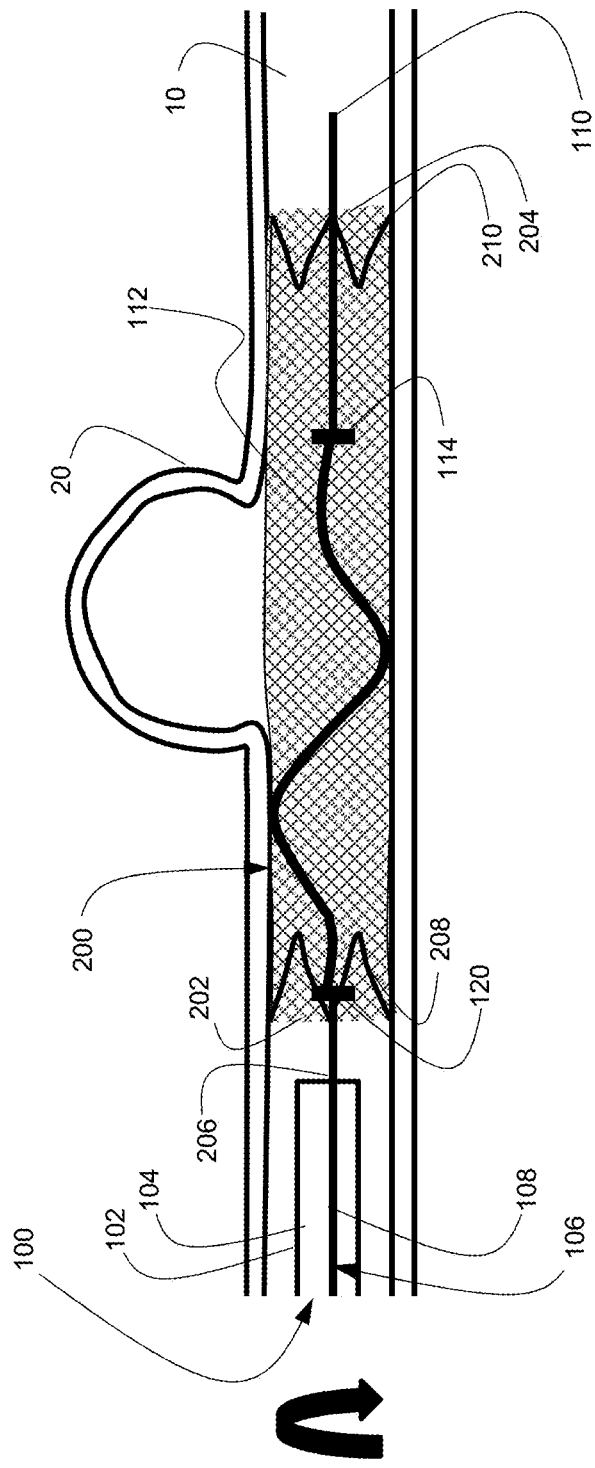

As illustrated in FIG. 2H, the delivery wire 106 can subsequently be rotated, and the shaped portion 112 can slide against portions of the braid, resulting in better conformity to the walls of the body lumen 10.

In the expanded configuration, as illustrated in FIG. 2H, the expandable element 200 can be expanded to conform to the dimensions of the patient's body lumen 10. The expanded dimension of the expandable element 200 allows the apparatus 100 to pass therethrough, to either advance to a second location or be withdrawn. The expandable element 200 can be expandable at least in part under its inherent proprieties, based at least on its original shape and the nature of the materials that make up the element, and further expanded by movement of the delivery wire 106 as described herein. Examples of the expandable element 200 can be one of pear shaped, ovoid, and elliptical when at its expanded diameter. The construction of the expandable element 200 is known to those of skill in the art. Other embodiments are contemplated for expandable elements 200 of this disclosure and can also be observed in U.S. Pat. Pub. 2016/0058524, a reference that is incorporated in its entirety herein.

Figure 3A:
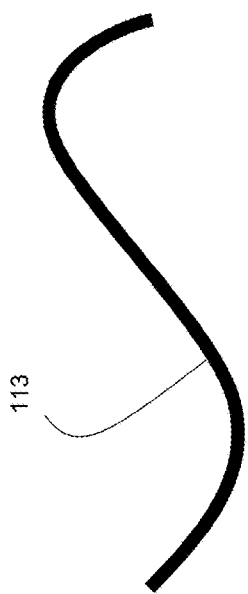
FIGS. 3A to 3C are drawings depicting shapes of a delivery wire portion according to the present invention.
Figure 3C:
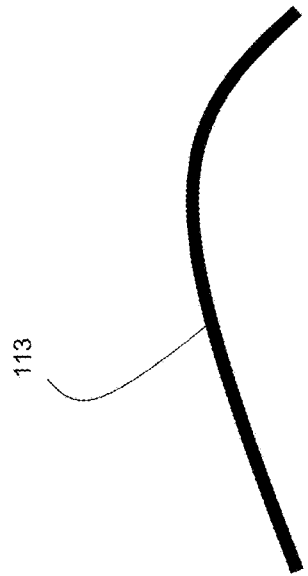
Figure 3B:
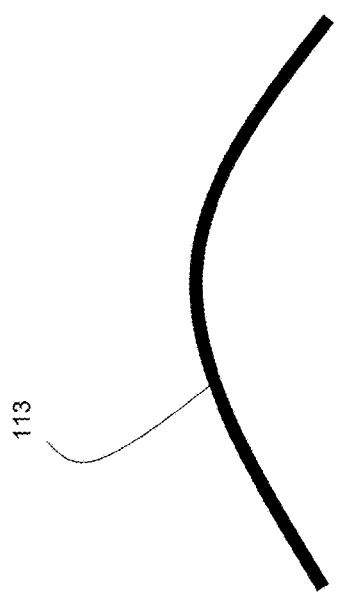

FIGS. 3A to 3C illustrate some potential shapes that a shapeable portion 112 of the delivery wire 106 can have when the expandable element is in a partially implanted configuration. Arced, curved, "S" and "C" shaped are some examples. In one example, the shapeable portion 112 presents an atraumatic section 113 to contact both the braided implant 200 and possibly the wall of the body lumen 10. This atraumatic section 113 minimizes damage to one or both of the implant 200 and lumen 10. Another example of an atraumatic section 113 is to minimize the amount of radial force applied once the shapeable portion 112 deforms from the straight to curved shape. Too much force, even applied by an atraumatic shape 113, can still damage the implant/lumen. Too little force or shape and the implant will not open to its full potential shape.

Figure 4:
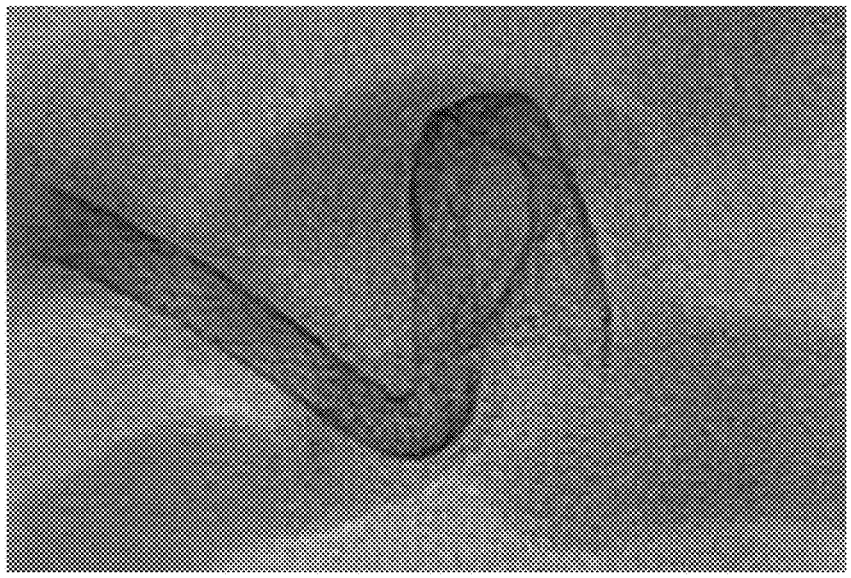
FIG. 4 is an image depicting a braided implant having a segment poorly apposed to a vessel wall as known in the art.

FIG. 4 depicts a braided implant having a segment poorly apposed to a vessel wall as known in the art. It is an object of the present invention to provide devices, systems, and methods of treatment for improving conformity of an implant to a vessel wall.

Figure 5:
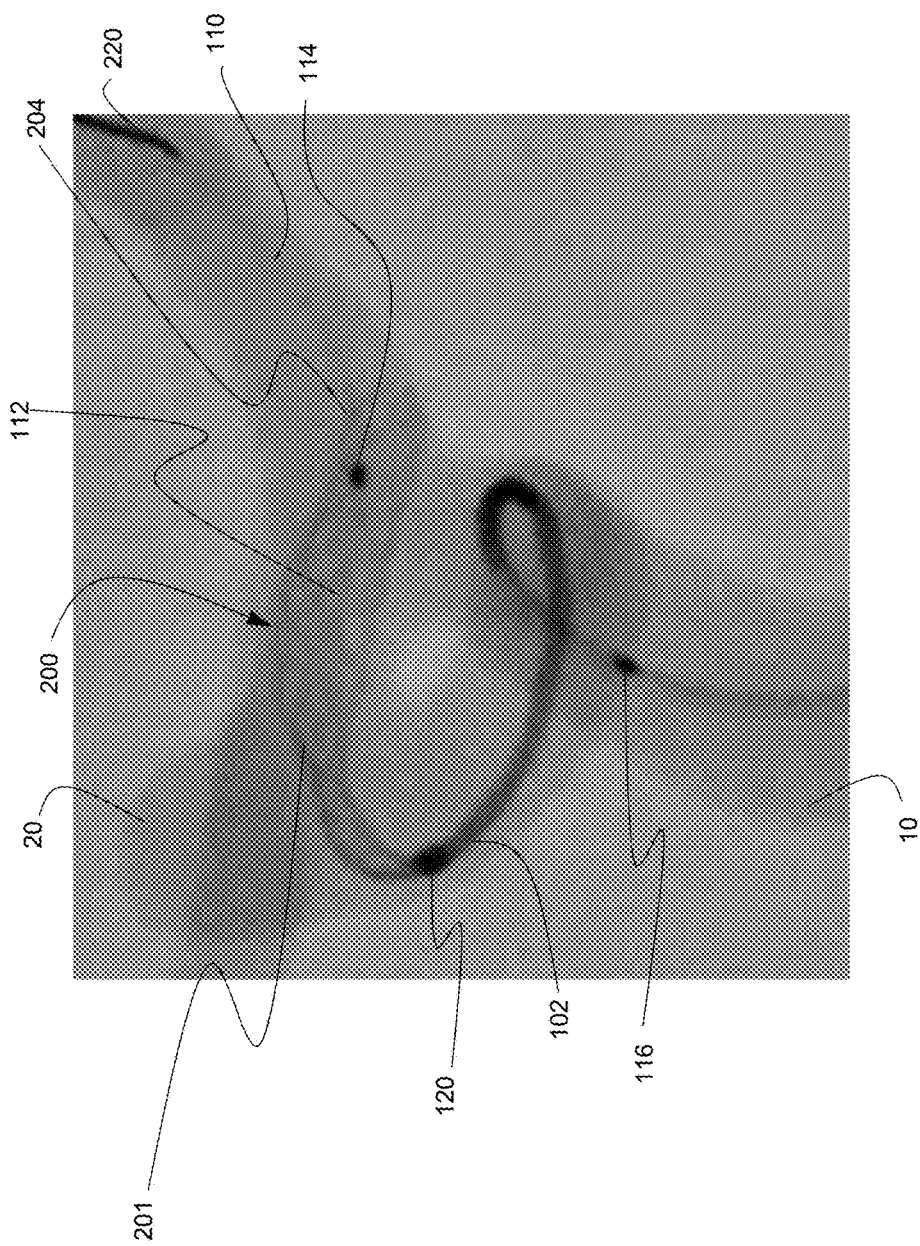
FIG. 5 is an image depicting an implantation system during implantation according to the present invention.

FIG. 5 depicts a partially implanted expandable element that is a braided implant 200 having a distal end 204 positioned outside a catheter 102 and a delivery wire 106 positioned inside the implant 200, the delivery wire 106 having a distal coil 220 positioned distal the implant 200, a distal bump 114 positioned inside the implant, a recapture bump 120 positioned inside the implant 200 proximal the distal bump 114, and proximal bump 116 positioned proximal the implant 200 inside the catheter 102. The implant 200 as depicted in FIG. 5 has a poorly apposed portion 201 that is not extended to conform to the vasculature 10.

FIGS. 6A to 6C illustrate movement of the delivery wire 106 within the system illustrated in FIG. 5 to provide an outward radial force from within the poorly apposed portion 201 and other portions of the implant 200 not fully apposed to the walls to move those portions closer to the walls of the vascular 10. Progressing from FIGS. 6A to 6B, the delivery wire 106 can be moved distally to extend against an outer curved portion of the implant 200 and/or to provide a pushing force by the proximal bump 116 against a proximal anchor (not shown) of the implant 200. Progressing from FIGS. 6B to 6C, the delivery wire 106 can be pulled proximally to press against an inner curved portion of the implant 200 and/or to retract at least a portion of the implant 200 into the catheter 102.

In the example illustrated in FIGS. 6A to 6C, the shaped portion 112 of the delivery wire 106 can be flexible to curve to the shape of a curved vasculature 10 and need not reshape as a result of being made from a memory shape material. The shapeable portion 112 can solely curve to conform to the shape of a curved bodily lumen such that distal and proximal movements of the expandable element 200, delivery wire 106, and catheter 102 can cause the delivery wire to move to provide a radial force from within the braided portion 206. In this example, the non-preshaped shapeable portion 112 can curve based on bringing the deliver wire 106 through the inside of the curve and the outside of a curve of a vasculature where the braided portion 206 is to be implanted.

Figure 7:
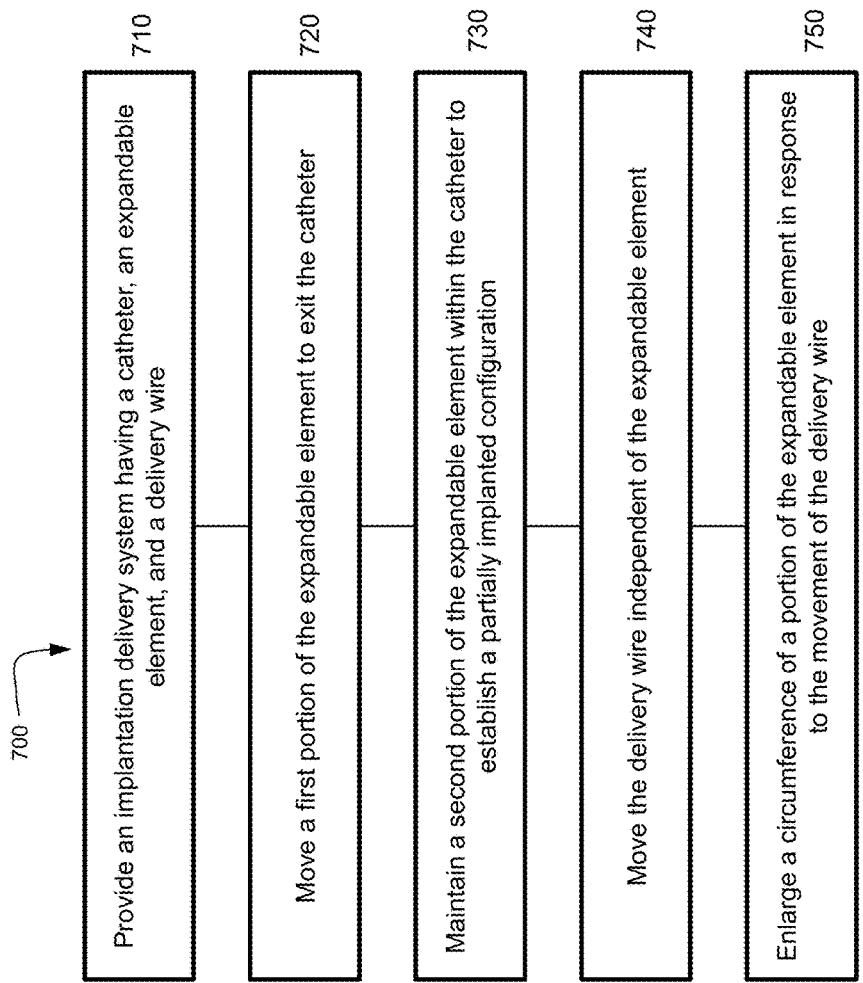
FIG. 7 is a flow diagram outlining example method steps for use of an apparatus or system for deploying an implant according to the present invention.

FIG. 7 is a flow diagram outlining example method steps for use of an apparatus or system for deploying an implant. The method steps can be implemented by an of the example means described herein or by any means that would be known to one of ordinary skill in the art.

Referring to method 700 illustrated in FIG. 7, in step 710 an implantation delivery system having a catheter, an expandable element, and a delivery wire can be provided. The implantation delivery system can be any of the delivery systems described herein having any combination of the features described here, as well as any features that would be known to one skilled in the art. In step 720 a first portion of the expandable element can be moved to exit the catheter. In step 730 a second portion of the expandable element can be maintained within the catheter to establish a partially implanted configuration. In step 740 the delivery wire can be moved independent of the expandable element in the partially implanted configuration. In step 750 a circumference of the expandable element can be enlarged in response to the movement of the delivery wire in step 740.

The descriptions contained herein are examples of embodiments of the invention and are not intended in any way to limit the scope of the invention. As described herein, the invention contemplates many variations and modifications of the implantation system and methods of use thereof, including various shapes of the shapeable portion of the delivery wire, various materials, various treatments, and various stent geometries. These modifications would be apparent to those having ordinary skill in the art to which this invention relates and are intended to be within the scope of the claims which follow.

The invention claimed is:

1. A vascular treatment apparatus, comprising:
   a catheter comprising an inner lumen;
   an expandable element comprising:
      a proximal end;
      a distal end;
      a braided portion located between the proximal end and the distal end;
      a proximal anchor member disposed at the proximal end;
      a distal anchor member disposed at the distal end;
      a compressed configuration dimensioned to fit within the inner lumen of the catheter; and
      a partially implanted configuration wherein the proximal end is dimensioned to fit within the inner lumen of the catheter and the distal end is dimensioned larger than the catheter; and
   a delivery wire disposed within and extending through the inner lumen and the expandable element, comprising:
      a proximal portion;
      a proximal bump member located at a distal end of the proximal portion;
      a distal portion;
      a distal bump member located at a proximal end of the distal portion; and
      a shapeable portion located between the proximal bump member and the distal bump member, the shapeable portion movable from a substantially straight configuration to a curved configuration upon exiting the inner lumen of the catheter,
      wherein the expandable element is movable from the compressed configuration to the partially implanted configuration by a distal movement of the delivery wire causing the distal bump member of the delivery wire to engage with the distal anchor member of the expandable element and push the distal anchor member distally, thereby expelling the distal anchor member from the catheter,
      wherein the delivery wire is movable distally, proximally, and rotationally in relation to the expandable element in the partially implanted configuration, and
      wherein the shapeable portion of the delivery wire is movable to provide a radial force from within the braided portion of the expandable element when the expandable element is in the partially implanted configuration.

2. The apparatus of claim 1 wherein the shapeable portion is movable to at least one of a symmetrical arc shape, an asymmetrical arc shape, an approximate "S" shape and an atraumatic shape in the curved configuration.

3. The apparatus of claim 1 wherein the apparatus is configurable as follows:
   the expandable element is in the compressed configuration and is positioned entirely within the inner lumen of the catheter,
   the shaped portion is in the substantially straight configuration and is positioned within a lumen of the braided portion of the expandable element,
   the distal bump member is positioned within the lumen of the braided portion of the expandable element, and
   the proximal bump member is positioned proximal the proximal anchor member.

4. The apparatus of claim 1 wherein the apparatus is configurable as follows:
   the expandable element is in the partially implanted configuration,
   the distal end of the expandable element is positioned outside the catheter,
   the proximal end and the proximal anchor of the expandable element are positioned within the inner lumen of the catheter, and
   the shapeable portion of the delivery wire is in the curved configuration and is positioned outside the catheter.

5. The apparatus of claim 4 wherein a rotation of the delivery wire in relation to the expandable element expands a radius of the expandable element.

6. A system for implanting a stent comprising:
   a catheter;
   a braided stent movable to a partially implanted configuration wherein a portion of the braided stent is exterior to the catheter and a portion of the braided stent is within the catheter; and
   a delivery wire movable independent of the braided stent and movable to provide a force to open the braided stent when the braided stent is in a partially implanted configuration;
      wherein the braided stent comprises a first expandable anchor at a distal end and a second expandable anchor at a proximal end,
      wherein the braided stent is movable in a compressed configuration through the catheter,
      wherein the braided stent is movable from the compressed configuration to the partially implanted configuration such that first expandable anchor is expanded in an implanted position distal to the catheter and the second expandable anchor is compressed within the catheter,
      wherein the delivery wire comprises a pusher bump and a shapeable segment,
      wherein the delivery wire is movable to extend through the braided stent when the braided stent is in the compressed configuration and when the braided stent is in the partially implanted configuration,
      wherein the pusher bump is movable to a position proximal the second expandable anchor when the braided stent is in the compressed configuration and when the braided stent is in the partially implanted configuration,
      wherein the shapeable segment is movable to a position within the braided stent when the braided stent is in the compressed configuration and when the braided stent is in the partially implanted configuration,
      wherein the shapeable segment is movable from a substantially straight configuration when the braided stent is in the compressed configuration to a curved configuration when the braided stent is in the partially implanted configuration, and
      wherein the shapeable segment is movable independent of the braided stent when the braided stent is in the partially implanted configuration.

7. The system of claim 6 wherein the pusher bump is movable to push the second expandable anchor distally thereby pushing the braided stent distally when the braided stent is in the partially implanted configuration.

8. The system of claim 6 wherein the delivery wire further comprises a puller bump movable to a position distal the pusher bump and the shapeable segment and positioned proximal the first expandable anchor when the braided stent is in the compressed configuration.

9. The system of claim 6 wherein the shapeable segment is movable to an arc shape in the curved configuration.

10. The system of claim 6 wherein the shapeable segment is movable to an undulating shape in the curved configuration.

11. The system of claim 6 wherein the delivery wire is movable in a distal direction, a proximal direction, and in a rotational direction independent of the braided stent when the braided stent is in the partially implanted configuration.

\* \* \* \* \*